(12) United States Patent
Brands

(10) Patent No.: US 6,552,239 B1
(45) Date of Patent: Apr. 22, 2003

(54) SYNTHESIS OF CYCLOPROPANEACETYLENE BY A ONE-POT PROCESS

(75) Inventor: Karel M. J. Brands, Jersey City, NJ (US)

(73) Assignee: Merck & Co., Inc., Rahway, NJ (US)

( * ) Notice: Subject to any disclaimer, the term of this patent is extended or adjusted under 35 U.S.C. 154(b) by 182 days.

(21) Appl. No.: 09/698,831

(22) Filed: Oct. 27, 2000

Related U.S. Application Data
(60) Provisional application No. 60/161,959, filed on Oct. 28, 1999.

(51) Int. Cl.[7] .................................................. C07C 1/32
(52) U.S. Cl. ...................... 585/358; 585/538; 585/359; 585/357; 585/325
(58) Field of Search ................................ 585/534, 538, 585/359, 357, 325

(56) References Cited

U.S. PATENT DOCUMENTS

| | | | |
|---|---|---|---|
| 5,519,021 A | | 5/1996 | Young et al. |
| 5,663,467 A | | 9/1997 | Thompson et al. |
| 5,856,492 A | | 1/1999 | Chen et al. |
| 5,922,864 A | | 7/1999 | Frey et al. |
| 5,952,537 A | * | 9/1999 | Stickley et al. ............. 585/534 |
| 5,955,627 A | * | 9/1999 | Nakazawa et al. .......... 560/124 |
| 6,028,237 A | * | 2/2000 | Parsons, Jr. ................. 585/359 |
| 6,180,835 B1 | * | 1/2001 | Asanuma et al. ............ 568/800 |
| 6,207,864 B1 | * | 3/2001 | Henningsen et al. ........ 568/348 |
| 6,297,410 B1 | * | 10/2001 | Fortunak et al. ............ 570/101 |
| 6,288,297 B1 | * | 11/2001 | Wang et al. ................. 585/538 |
| 6,313,364 B1 | * | 11/2001 | Brands ........................ 585/534 |
| 6,359,164 B1 | * | 3/2002 | Wang et al. ................. 558/371 |

FOREIGN PATENT DOCUMENTS

| | | |
|---|---|---|
| WO | WO 95/20389 | 8/1995 |
| WO | WO 96/37457 | 11/1996 |
| WO | WO 98/30543 | 7/1998 |

OTHER PUBLICATIONS

P. Callant et al., "An Efficient Preparation and the Intramolecular Cyclopropanation of Alpha–Diazo–Beta–Ketophosphonates and Alpha–Diazophosphonoacetates", Synthetic Communications, vol. 14, No. 2, pp. 155–161 (1984) no month.

T. Kuwayama et al., "Preparation of Cyclopropylacetylenes", Chemical Abstract 130:209445 (1999) Abstract of JP11060513 no month.

T. Kuwayama et al., "Production of Cyclopropylacetylene Derivative", Patent Abstracts of Japan (Abstract of JP11060513 which published on Mar. 3, 1999).

C. Hudson, et al., "A Quantitative Analysis of Cyclopropyl Beta Hyperfine Splittings", Journal of the American Chemical Society, vol. 94:4, pp. 1158–1163, (Feb. 23, 1972).

H. Miltzer, et al., "Versatile Syntheses of Alkynyl–and Substituted Alkynlcyclopropanes: 2–Alkoxyethynylcyclopropanes for the Anellation of Bicyclo[3.3.0]octane Fragments", Synthesis, pp. 998–1012, (1993) no month.

A. Thompson et al., "Use of an Ephedrine Alkoxide to Mediate Enantioselective Addition of an Acetylide to a Prochiral Ketone: Asymmetric Synthesis of the Reverse Transcriptase Inhibitor L–743, 726", Tetrahedron Letters, vol. 36, No. 49, pp. 8937–8940, (1995) no month.

J. Salaun, "Preparation and Substituent Effect in the Solvolysis of 1–Ethynylcyclopropyl Tosylates", J. Org. Chem., vol. 41, No. 7, pp. 1237–1240, (1976) no month.

F. Carey et al., "Silicon–Containing Carbanions. II. Ketene Thioacetal Synthesis via 2–Lithio–2–trimethylsilyl–1, 3–dithiane", J. Org. Chem., vol. 37, No. 12, pp. 1926–1929, (1972) no month.

H. Takeshita et al., "Sensitized Photoreduction of Dioxetanes to cis–1,2–Glycols: Solvent and Sensitizer Dependencies on the Singlet Oxygen Oxidation", J. Org. Chem., vol. 43, No. 15, pp. 3080–3083 (1978) no month.

D.J. Peterson, "A Carbonyl Olefination Reaction Using Silyl–Substituted Organometallic Compounds", J. Org. Chem., vol. 33, No. 2, pp. 780–784 (1968) no month.

S. Ohira, "Methanolysis of Dimethyl (1–Diazp–2–Oxopropyl)Phosphonate: Generation of Dimethyl (Diazomethyl) Phosphonate and Reaction with Carbonyl Compounds", Synthetic Comm., vol. 19 Nos. 3&4, pp. 561–564 (1989) no month.

S. Muller et al., "An Improved One–Pot Procedure for the Synthesis of Alkynes from Aldehydes" Synlett., pp. 521–522 (1996) no month.

Chemical Abstracts No. 78:124091, abstract of W. Schoberth et al., "Eine Einfache Herstellungsmethode fur Cyclopropylacetylen", Synthesis, p. 703, (1972) no month.

L. A. Akopyan et al., "Catalytic Decarboxylation of Alpha–Acetylenic Acids", J. of General Chemistry, vol. 44, No. 8, Part 2, p. 1804 (1974) no month.

* cited by examiner

Primary Examiner—Nadine G. Norton
(74) Attorney, Agent, or Firm—Kenneth R. Walton; Valerie J. Camara

(57) ABSTRACT

The present invention relates to a process for the preparation of cyclopropaneacetylene by reacting a ketophosphonate with a diazo-transfer reagent in the presence of non-nucleophilic base in an aprotic solvent to generate a reaction mixture containing a ketodiazophosphonate compound and then reacting the reaction mixture with cyclopropanecarboxaldehyde in a non-nucleophilic base and a protic solvent to yield cyclopropaneacetylene.

20 Claims, No Drawings

SYNTHESIS OF CYCLOPROPANEACETYLENE BY A ONE-POT PROCESS

This application claims the benefit of Provisional application Ser. No. 60/161,959 filed Oct. 28, 1999.

FIELD OF THE INVENTION

The present invention relates to a process for the preparation of cyclopropaneacetylene (CPA) by a one-pot process.

BACKGROUND OF THE INVENTION

A retrovirus designated human immunodeficiency virus (HIV) is the etiological agent of the complex disease that includes progressive destruction of the immune system (acquired immune deficiency syndrome, AIDS) and degeneration of the central and peripheral nervous system. A common feature of retrovirus replications is reverse transcriptase to generate DNA copies of HIV sequences, a required step in viral replication. It is known that some compounds are reverse transcriptase inhibitors and are effective agents in the treatment of AIDS and similar diseases, e.g., azidothylmidine or AZT.

Cyclopropaneacetylene (CPA) is a key raw material for the preparation of an inhibitor of HIV reverse transcriptase, which is known as DMP-266 having a chemical name of (−)6-chloro-4-cyclopropylenthynyl-4-trifluoromethyl-1,4-dihydro-2H-3,1-benzoxanzin-2-one.

The synthesis of DMP-266 and structurally similar reverse transcriptase inhibitors are disclosed in U.S. Pat. No. 5,519,021, and the corresponding PCT International Patent Application WO 95/20389, which published on Aug. 3, 1995. Additionally, the asymmetric synthesis of an enantiometric benzoxazinone by a highly enantioselective acetylide addition and cyclization sequence has been described by Thompson, et. al., *Tetrahedron Letters* 1995, 36, 8937–8940, as well as the PCT publication, WO 96/37457, which published on Nov. 28, 1996.

In addition, various aspects of the synthesis of DMP-266 have been disclosed in the United States Patents. U.S. Pat. No. 5,663,467 discloses a synthesis of CPA involving cyclization of 5-halo-1-pentyne in base. U.S. Pat. No. 5,856,492 discloses a synthesis of a chiral mediator, and U.S. Pat. No. 5,922,864 discloses an efficient method to prepare DMP-266 by a cyclization reaction. A process for making chiral alcohol is published on Jul. 16, 1998 in PCT Publication No. WO 98/30543.

Several methods have been described in published literature for preparation of cyclopropaneacetylene. C. E. Hudson and N. L. Bauld, *J. Am. Chem. Soc.* 94:4, p. 1158 (1972); J. Salaun, *J. Org. Chem.* 41:7, p. 1237 (1976); and W. Schoberth and M. Hanack, *Synthesis* p. 703 (1972), disclose methods for the preparation of cyclopropylacetylene by dehydrohalogenating 1-cyclopropyl-1,1-dichloroethane. Miltzer, H. C. et al., *Synthesis*, 998 (1993) disclose a method for preparation of cyclopropylalkenes by halogenating an enolether, reacting the alkyl 1,2-dihaloether with propargyl magnesium bromide, and cyclizing to give a 2-alkoxy-1-ethynylcyclopropane. F. A. Carey and A. S. Court, *J. Org. Chem.*, Vol. 37, No. 12, p. 1926 (1972) disclose the use of a modified Wittig-Horner olefin synthesis for organic transformations. D. J. Peterson, *J. Org. Chem.*, Vol. 20C, No. 33, p. 780 (1968) describes the application of olefination to make vinyl sulfides and H. Takeshita and T. Hatsui, *J. Org. Chem.* Vol. 43, No. 15, p. 3083 (1978) disclose the use of potassium 3-aminopropylamide in base-catalyzed prototropic reactions.

However, the currently available ways to prepare CPA can result in poor yield and often have problems with impurities in the final product. Ohira, S., *Synth. Comm.*, 1989, 561–564 and Müller, S. et al., *Synlett*, 1996, 521–522 describe an in-situ preparation of dimethyldiazomethylphosphonate and its use for the conversion of aldehydes into terminal acetylenes. The precursor for the in situ preparation of the dimethyldiazomethylphosphonate is dimethyl (1-diazo-2-oxopropyl)phosphonate. This reagent in turn is prepared from commercially available dimethyl (2-oxopropyl) phosphonate. The latter reaction is typically performed using a sulfonyl azide derivative as diazo transfer reagent followed by a difficult chromatographic purification of the dimethyl (1-diazo-2-oxopropyl)phosphonate product. Without purification, the crude dimethyl (1-diazo-2-oxopropyl) phosphonate product converts cyclopropanecarboxaldehyde to CPA in poor yield due to a reaction of the intermediate dimethyldiazomethylphosphonate with the sulfonamide by-product corresponding to the diazo transfer reagents. As a result of this need for purification, published methods are not suitable for a practical one-pot synthesis of CPA from cyclopropanecarboxaldehyde.

In view of above, there is a need for an alternative practical way to prepare CPA, and thus the objective of the present invention is to provide an efficient and practical way to produce CPA by a one-pot process.

SUMMARY OF THE INVENTION

The present invention relates to a process for the preparation of cyclopropaneacetylene comprising the steps of: (a) reacting a ketophosphonate compound of Formula I,

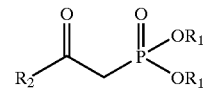

Formula I with a diazo-transfer reagent, $[(R)_2N]_3P^+N_3X^-$, wherein R is $C^1$–$C_5$ alkyl, in the presence of a catalytic amount of a first non-nucleophilic base in an aprotic solvent to generate a reaction mixture containing ketodiazophosphonate compound of Formula II;

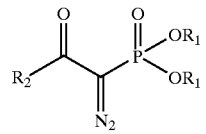

Formula II wherein $R_1$ and $R_2$ substituents in Formulae I and II independently are: $C_1$–$C_6$ alkyl, or aryl, wherein aryl is defined as phenyl or naphthyl which is unsubstituted or substituted with one or two substituents selected from the group consisting of: Cl, F, Br, I, $(C_1$–$C_4)$-alkyl, —O—$(C_1$–$C_4)$-alkyl, —$NO_2$, —OH, $CF_3$, $(C_1$–$C_4)$-alkoxy, $S(O)_x$—$(C_1$–$C_4)$-alkyl, —$N(R)_2$, —COOR, and $CON(R)_2$, wherein R is H, $(C_1$–$C_6)$-alkyl, phenyl, or $(C_1$–$C_6)$-alkylphenyl, and X is 0, 1, or 2; and (b) reacting the reaction mixture containing the ketodiazophosphonate compound of Formula II with cyclopropanecarboxaldehyde using a second non-nucleophilic base and a protic solvent to yield the cyclopropaneacetylene.

DETAILED DESCRIPTION OF THE INVENTION

The present invention is directed to a process for the preparation of cyclopropaneacetylene (CPA) by a one-pot process as shown below:

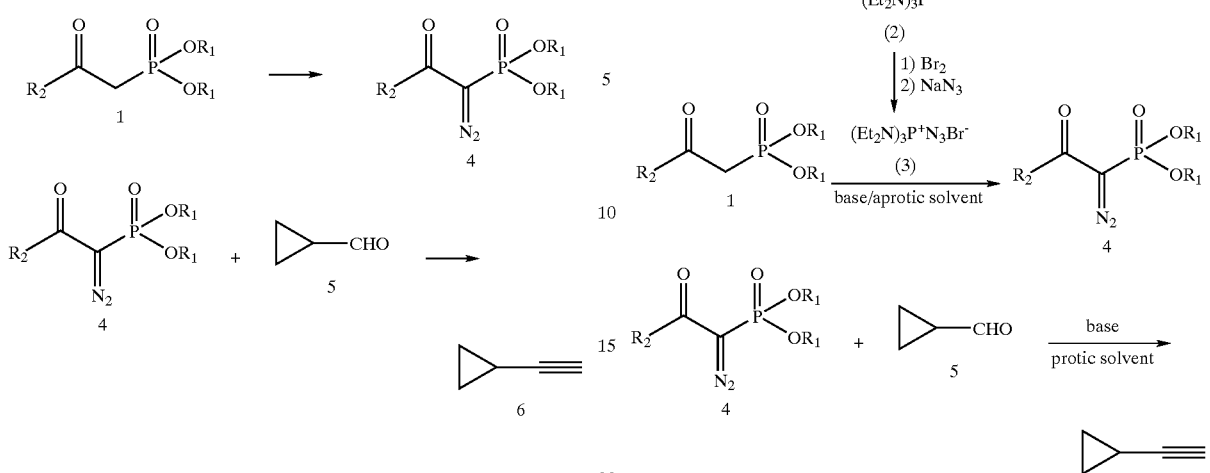

$R_1$ and $R_2$ substituents independently are: $C_1$–$C_6$ alkyl, and aryl, wherein aryl is defined as phenyl or naphthyl which is unsubstituted or substituted with one or two substituents selected from the group consisting of: Cl, F, Br, I, ($C_1$–$C_4$)-alkyl, —O—($C_1$–$C_4$)-alkyl, —NO2, —OH, $CF_3$, ($C_1$–$C_4$)-alkoxy, $S(O)_x$—($C_1$–$C_4$)-alkyl, —$N(R)_2$, —COOR, and $CON(R)_2$, wherein R is H, ($C_1$–$C_6$)-alkyl, phenyl, or ($C_1$–$C_6$)-alkylphenyl, and X is 0, 1, or 2. A dialkyl β-keto-α-diazophosphonate (4) is generated from the corresponding dialkyl β-keto-phosphonate (1) by diazo transfer and then directly used to convert cyclopropanecarboxaldehyde (5) into CPA (6).

Azidotris(diethylamino)phosphonium bromide (3) can be synthesized from $PCl_3$, diethylamine, and $NaN_3$ via hexaethylphosphorous triamide by using established methods. See McGuinness, M. et al., *Tetrahedron Letters*, 1990, 4987–4990. It also has been reported that dialkyl β-keto-α-diazophosphonate (4) can be prepared by using a sulfonyl azide as a diazo transfer reagent, such as $CH_3SO_2N_3$ or dodecyl benzene sulfonyl azide. See Ohira, S., *Synth. Comm.*, 1989, 561–564; and Müller, S. et al., *Synlett*, 1996, 521–522. However, the direct use of dialkyl β-keto-α-diazophosphonate (4) prepared with sulfonyl azides to convert cyclopropanecarboxaldehyde (5) to CPA (6) results in an unacceptably poor yield. This is caused by a cooperative deleterious effect of both the solvent and sulfonamide by-product corresponding to the diazo transfer reagents. Therefore to avoid this problem, the currently available method requires a cumbersome isolation of crude dialkyl β-keto-α-diazophosphonate (4) before reacting it with cyclopropanecarboxaldehyde (5) to produce CPA (6).

On the contrary, the present invention relates to a one-pot synthesis of CPA (6) involving the direct use of crude dialkyl β-keto-α-diazophosphonate (4) without further purification or isolation. When dialkyl β-keto-α-diazophosphonate (4) is prepared from dialkyl β-keto-phosphonate (1) and azidotris (diethylamino)phosphonium bromide (3), it can be directly used to react with cyclopropanecarboxaldehyde (5) to produce the desired product, CPA (6), in good yield. As a result, the present invention eliminates isolation of the intermediate βketo-α-diazophosphonate (4).

A synthesis of CPA by a one-pot process can be achieved by either starting from the commercial azidophosphonium salt (3) or from an alkyl phosphorous triamide, preferably hexaethyl phosphorous triamide (2) as shown below, and preparing (3) in the same pot.

$R_1$ and $R_2$ substituents independently are: $C_1$–$C_6$ alkyl, and aryl, wherein aryl is defined as phenyl or naphthyl which is unsubstituted or substituted with one or two substituents selected from the group consisting of: Cl, F, Br, I, ($C_1$–$C_4$)-alkyl, —O—($C_1$–$C_4$)-alkyl, —NO2, —OH, $CF_3$, ($C_1$–$C_4$)-alkoxy, $S(O)_x$—($C_1$–$C_4$)-alkyl, —$N(R)_2$, —COOR, and $CON(R)_2$, wherein R is H, ($C_1$–$C_6$)-alkyl, phenyl, alkylphenyl, and X is 0, 1, or 2.

Diazo transfer from azidotris(diethylamino)phosphonium bromide (3) to keto phosphonate compound (1), preferably dimethyl 2-oxopropyl phosphonate, yielding dialkyl β-keto-α-diazophosphonate (4) is achieved with a catalytic amount of a first non-nucleophilic base, preferably 1–5% of 1,8-diazabicyclo[5.4.0]undec7-ene (DBU) in an aprotic solvent, preferably acetonitrile or DMF, and most preferably acetonitrile. It is noted that these conditions as discussed above are not successful when sulfonyl azides are used as diazo transfer reagents. The resulting solution of dialkyl β-keto-α-diazophosphonate (4) can be directly used for the conversion of cyclopropanecarboxaldehyde (5) to CPA (6) in the presence of a second non-nucleophilic base and protic solvent, preferably $K_2CO_3$ and $CH_3OH$, respectively.

For the one-pot synthesis of CPA starting from the azidophosphonium salt (3), a catalytic amount of a first non-nucleophilic base, preferably 1,8-diazabicyclo[5.4.0]undec-7-ene (DBU) was added to a solution of keto phosphonate (1), preferably dimethyl 2-oxopropyl phosphonate, and azidotris(diethylamino)phosphonium bromide (3) in an aprotic solvent, preferably dry acetonitrile, at a temperature between about −20° C. and about room temperature (20° C.–25° C.). Upon contact with the first non-nucleophilic base, the reaction mixture is allowed to stand at a temperature of about −20° C. to about +25° C., preferably about −10° C. to about −20° C., for time sufficient for the reaction to occur, generally from about an hour to about two hours. Subsequently, the reaction mixture is added to a solution of cyclopropanecarboxaldehyde (5) in a protic solvent and a second non-nucleophilic base, preferably dry methanol and potassium carbonate, respectively. The resulting mixture is then diluted with water and extracted with alkane solvent, preferably n-octane, and CPA (6) was obtained by a distillation at atmospheric pressure.

Alternatively, CPA can be synthesized by the one-pot process starting from an alkyl phosphorous triamide, preferably hexaethyl phosphorous triamide (2). To a solution of a halogenating agent in an aprotic solvent, preferably $Br_2$ and dry acetonitrile respectively, at a temperature of about −20° C. to about +25° C., preferably about −10° C. to about −20° C., is added slowly alkyl phosphorous triamide, preferably hexaethyl phosphorous triamide (2), at such a rate that the temperature was maintained below about +10° C. After the reaction mixture stands for about at least ten minutes, alkali metal azide, preferably sodium azide (NaN$_3$), is added in one portion and the resulting suspension was allowed to warm to room temperature for at least about two hours. After cooling to a temperature about −10° C. to about −20° C., preferably about −15° C., keto phosphonate (1), preferably dimethyl 2-oxopropyl phosphonate, and a catalytic amount of a first non-nucleophilic base, preferably 1,8-diazabicyclo[5.4.0]undec-7-ene (DBU), are added. The solids are then filtered when the reaction is completed, after about an hour to about two hours, and washed with a minimal amount of aprotic solvent, preferably acetonitrile. Then, a solution of cyclopropanecarboxaldehyde (5) in protic solvent, preferably dry methanol, and a second non-nucleophilic base, preferably potassium carbonate, are added to the filtrates and the resulting reaction mixture is stirred at room temperature for time sufficient to complete the reaction, generally for about 15 hours to about 25 hours. The crude slurry of dialkyl β-keto-α-diazophosphonate (4) can also be reacted directly with cyclopropanecarboxaldehyde (5) without the filtration. After completion of the reaction the reaction mixture is cooled to about 0° C. and diluted with ice-cold water and extracted with alkane solvent, preferably n-octane. The combined extracts are washed with water and a solution of CPA (6) is obtained which can be used as such or pure CPA is isolated via a distillation at atmospheric pressure.

The yield of CPA obtained by the present invention by a one-pot process as discussed above is found to be dependent on the ratio of solvents and reagents present in the reaction mixture as shown below in the Table 1.

TABLE 1

CPA yield based on a solvent and a reagent ratio

| Entry | Starting Material | Solvent Ratio | Reagent Ratio[a] | Assay Yield[b] by GC |
|---|---|---|---|---|
| 1 | 3 | CH$_3$CN/CH$_3$OH 1.0/7.5 | 3/1/5 1.2/1.2/1.0 | 95 |
| 2 | 3 | DMF/CH$_3$OH 1.0/7.5 | 3/1/5 1.1/1.1/1.0 | 74 |
| 3 | 2 | CH$_3$CN/CH$_3$OH 1.0/3.8 | 2/Br$_2$/NaN$_3$/1/5 1.3/1.2/1.6/1.2/1.0 | 60 |
| 4[c] | 2 | CH$_3$CN/CH$_3$OH 1.0/13.3 | 2/Br$_2$/NaN$_3$/1/5 1.4/1.3/1.4/1.2/1.0 | 73 |
| 5[c] | 2 | CH$_3$CN/CH$_3$OH 1.0/2.6 | 2/Br$_2$/NaN$_3$/1/5 1.4/1.3/1.4/1.2/1.0 | 58 |

[a]In all cases 5 mol % of DBU and 200 mol % of K$_2$CO$_3$ relative to 5 were used.
[b]CPA yield based on starting aldehyde 5
[c]Slurry of crude 4 in CH$_3$CN was filtered before addition of CH$_3$OH, 5 and K$_2$CO$_3$ It is noted that a solvent system of acetonitrile/methanol is preferred over DMF/methanol. Additionally the ratio of aprotic solvent to protic solvent and the ratio of reagents present in the reaction mixture influence the overall yield of CPA by the one-pot process. The ratio of aprotic solvent to protic solvent can be in the range of about 1:1 to about 1:20, preferably about 1:1 to about 1:14.

The yield of CPA obtained by a one-pot process as discussed above is also found to be dependent on the amount of second non-nucleophilic base used as well as the nucleophilicity of the protic solvent, as shown below in the Table 2.

TABLE 2

CPA yield based on the amount of a second base and an alcoholic solvent

| Entry | (a)/(b) Molar Ratio | Second Base | Protic Solvent | Assay Yield of CPA |
|---|---|---|---|---|
| 1 | 1.0/1.2 | 1.0 eq. K$_2$CO$_3$ | CH$_3$OH | 63 |
| 2 | 1.0/1.2 | 2.0 eq. K$_2$CO$_3$ | CH$_3$OH | 90 |
| 3 | 1.0/1.2 | 4.0 eq. K$_2$CO$_3$ | CH$_3$OH | 89 |
| 4 | 1.0/1.2 | 2.0 eq. K$_2$CO$_3$ | n-propanol | 43 |
| 5 | 1.0/1.2 | 0.1 eq. Et$_3$N | CH$_3$OH | 0 |

(a) is cyclopropanecarboxaldehyde
(b) is β-keto-α-diazo-phosphonate.

It is found that the amount of a second non-nucleophilic base may be present in the reaction mixture in amounts between about 1.0 equivalent to about 4.0 equivalents relative to the amount of cyclopropanecarboxaldehyde, preferably about 2 equivalents to about 4 equivalents. When triethylamine is used as a second non-nucleophilic base, no CPA is produced. With respect to the protic solvent, methanol is preferred over propanol.

For the purpose of this invention, the aprotic solvent is selected from the group consisting of tetrahydrofuran (THF), acetonitrile, dimethylformamide (DMF), dimethylacetamide (DMA), N-methylpyrrolidinone (NMP), diethyl ether, dichloromethane, chloroform, ethyl acetate, pentane, hexane, toluene, benzene, chlorobenzene, methyl tert-butyl ether (MTBE) and mixtures thereof. The preferred aprotic solvent is acetonitrile. The term aprotic solvent means a type of solvent which neither donates nor accepts protons.

The protic solvents of the present invention include alcoholic solvents and water, which are selected from the group consisting of $C_1$–$C_6$ alcohol, H$_2$O, and mixtures thereof. The preferred protic solvent is $C_1$–$C_6$ alcohol, and methanol is most preferred.

The ratio of aprotic solvent to protic solvent in the reaction mixture is between about 1:1 and about 1:20, preferably about 1:1 and about 1:14. The preferred aprotic/protic solvent mixture is acetonitrile/methanol.

The first non-nucleophilic base used in the present invention is selected from the group consisting of 1,8-diazabicyclo[5.4.0]undec7-ene (DBU), potassium tert-butoxide, tetramethylguanine (TMG), and mixtures thereof. The preferred first non-nucleophilic base is a catalytic amount of DBU, preferably 1–5% of DBU in aprotic solvent.

The second non-nucleophilic base used in the present invention is selected from alkali metal carbonates or alkali metal hydroxides, which is selected from the group consisting of cesium carbonate, potassium carbonate, sodium carbonate, lithium carbonate, cesium hydroxide, potassium hydroxide, sodium hydroxide, and lithium hydroxide. The preferred second non-nucleophilic base is potassium carbonate. The second non-nucleophilic base may be present in the reaction mixture in amounts between about 1.0 equivalent to about 4.0 equivalents relative to the amount of cyclopropanecarboxaldehyde, preferably between about 2.0 and about 4.0 equivalents.

The alkyl phosphorous triamide used in the present invention is (R$_2$N)$_3$P, wherein R is $C_1$–$C_5$ alkyl.

The halogenating agent used in the present invention is selected from the group consisting of bromine, chlorine, iodine, N-bromosuccinimide, N-chlorosuccinimide.

The alkyl metal azide used in the present invention is selected from the group consisting of NaN$_3$, LiN$_3$, and mixtures thereof.

Relatively pure CPA as a solution in organic solvent, preferably alkane solvent, can be obtained by dilution of the alcoholic solution with an equal volume of water followed by extractions with organic solvent, preferably alkane solvent which includes hexane, octane and decane.

The reagents use in the present invention are either commercially available or may be prepared by synthetic methods commonly known in the art. The following examples are intended to illustrate the present invention but are not intended to limit the reasonable scope thereof. Examples 1–3 illustrate the preparation of the desired product, CPA, using a one-pot process starting with either azidophosphonium salt or hexaethylphosphoroustriamide.

Reaction Scheme

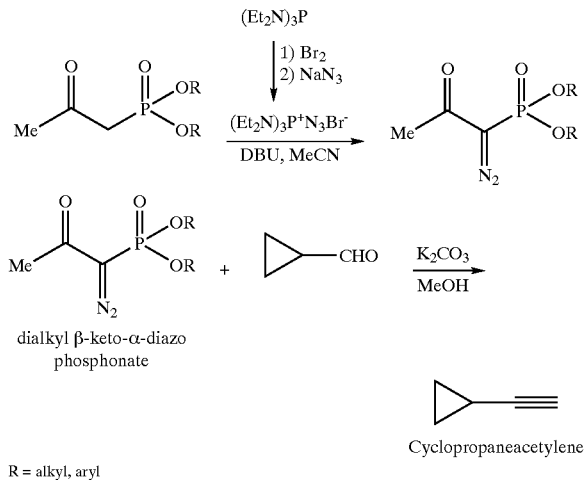

R = alkyl, aryl

Alkyl and aryl substituents are: $C_1$–$C_6$ alkyl, and aryl, wherein aryl is defined as phenyl or naphthyl which is unsubstituted or substituted with one or two substituents selected from the group consisting of: Cl, F, Br, I, ($C_1$–$C_4$)-alkyl, —O—($C_1$–$C_4$)-alkyl, —NO$_2$, —OH, CF$_3$, ($C_1$–$C_4$)-alkoxy, S(O)$_x$—($C_1$–$C_4$)-alkyl, —N(R$_1$)$_2$, —COOR$^1$, and CON(R$^1$)$_2$, wherein R$^1$ is H, ($C_1$–$C_6$)-alkyl, phenyl, or ($C_1$–$C_6$)-alkylphenyl, and X is 0, 1, or 2.

EXAMPLE 2

One-pot CPA Synthesis Starting From the Azidophosphonium Salt

To a solution of dimethyl 2-oxopropyl phosphonate (2.10 g; 12.0 mmol) and azidotris(diethylamino)phosphonium bromide (4.48 g; 11.9 mmol) in dry acetonitrile (10 mL) at about −15° C. was added 1,8-diazabicyclo[5.4.0]undec7-ene (90 μL; 0.6 mmol) in one portion. The reaction mixture was aged for about an hour at about −15° C. and then added to a solution of cyclopropanecarboxaldehyde (0.71 g; 10.13 mmol) in dry methanol (50 mL) in a sealed flask. After addition of potassium carbonate (3.30 g; 23.9 mmol) the mixture was stirred at room temperature overnight. The resulting mixture was diluted with 100 mL of water and extracted with n-octane (3×50 mL). The combined extracts were washed with water (50 mL) and assayed by Gas Chromatography (GC) to contain 635 mg of CPA (95% assay yield from aldehyde to acetylene). CPA was obtained via distillation of the n-octane solution at atmospheric pressure.

EXAMPLE 3

One-pot CPA Synthesis Starting From Hexaethylphosphoroustriamide

To a solution of bromine (5.03 g; 31.5 mmol) in dry acetonitrile (20 mL) at about −15° C. was added slowly hexaethyl phosphorous triamide (8.43 g; 34.1 mmol) at such a rate that the temperature was maintained below about +10° C. After aging for about 10 minutes, sodium azide (2.25 g; 34.2 mmol) was added in one portion and the resulting suspension was allowed to warm to room temperature over 2 hours. After cooling to about −15° C., dimethyl 2-oxopropyl phosphonate (5.55 g; 28.6 mmol) and 1,8-diazabicyclo[5.4.0]undec7-ene (100 μL; 0.65 mmol) were added. The solids were filtered after about 45 minutes and washed with a minimal amount of acetonitrile. Then, a solution of cyclopropanecarboxaldehyde (1.72 g; 24.5 mmol) in dry methanol (200 mL) and potassium carbonate (8.00 g; 57.8 mmol) were added and the resulting mixture stirred at room temperature for about 16 hours. The reaction mixture was cooled to about 0° C. and diluted with 250 mL of ice-cold water and extracted with n-octane (3×30 mL). The combined extracts were washed with water (30 mL) and assayed to contain 1192 mg of CPA (73% assay yield from aldehyde to acetylene). CPA was obtained via distillation of the n-octane solution at atmospheric pressure.

What is claimed is:

1. A process for the preparation of cyclopropaneacetylene comprising the steps of:

(a) reacting a ketophosphonate compound of Formula I,

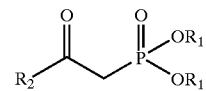

Formula I with a diazo-transfer reagent, $[(R^*)_2N]_3P^+N_3X^-$, wherein R* is $C_1$–$C_5$ alkyl and X$^-$ is halide, in the presence of a catalytic amount of a first non-nucleophilic base in an aprotic solvent to generate a reaction mixture containing ketodiazophosphonate compound of Formula II;

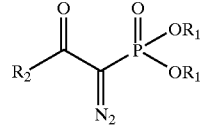

Formula II wherein R$_1$ and R$_2$ substituents in Formulae I and II independently are: $C_1$–$C_6$ alkyl or aryl, wherein aryl is defined as phenyl or naphthyl which is unsubstituted or substituted with one or two substituents selected from the group consisting of: Cl, F, Br, I, ($C_1$–$C_4$)-alkyl, —O—($C_1$–$C_4$)-alkyl, —NO$_2$, —OH, CF$_3$, ($C_1$–$C_4$)-alkoxy, S(O)$_x$—($C_1$–$C_4$)-alkyl wherein x is 0, 1, or 2, —N(R)$_2$, —COOR, and CON(R)$_2$, wherein R is H, ($C_1$–$C_6$)-alkyl, phenyl, or ($C_1$–$C_6$)-alkylphenyl; and (b) reacting the reaction mixture containing the ketodiazophosphonate compound of Formula II with cyclopropanecarboxaldehyde using a second non-nucleophilic base and a protic solvent to yield the cyclopropaneacetylene.

2. The process of claim 1, wherein the ketophosphonate compound is dimethyl 2-oxopropylphosphonate.

3. The process of claim 2, wherein the diazo-transfer reagent is azidotris(diethylamino)phosphonium bromide, $[(CH_3CH_2)_2N]_3P^+N_3Br^-$.

4. The process of claim 3, wherein the diazo-transfer reagent, $[(CH_3CH_2)_2N]_3P^+N_3Br^-$, is generated from hexaethyl phosphorous triamide, $[(CH_3CH_2)_2N]_3P$, by consecutive reactions with bromine (Br$_2$) and sodium azide (NaN$_3$)

in aprotic solvent at a temperature between about −20° C. and about +25° C.

5. The process of claim 4, wherein the aprotic solvent is selected from the group consisting of tetrahydrofuran, acetonitrile, dimethylacetamide, dimethylformamide, N-methylpyrrolidinone, diethyl ether, dichloromethane, chloroform, ethyl acetate, pentane, hexane, toluene, benzene, chlorobenzene, methyl tert-butyl ether, and mixtures thereof.

6. The process of claim 5, wherein the aprotic solvent is acetonitrile.

7. The process of claim 6, wherein the first non-nucleophilic base is selected from the group consisting of 1,8-diazabicyclo[5.4.0]undec7-ene, potassium tert-butoxide, tetramethylguanine, and mixtures thereof.

8. The process of claim 7, wherein the first non-nucleophilic base is 1,8-diazabicyclo[5.4.0]undec7-ene.

9. The process of claim 8, wherein the first non-nucleophilic base is about 1 mol % to about 5 mol % of 1,8-diazabicyclo[5.4.0]undec-7-ene, based on starting ketophosphonate I, in aprotic solvent.

10. The process of claim 9, wherein the reaction mixture of step (a) is allowed to stand at a temperature between about −20° C. and about +25° C. for about an hour to about two hours upon contact with the 1,8-diazabicyclo[5.4.0]undec-7-ene.

11. The process of claim 10, wherein the second non-nucleophilic base is selected from the group consisting of alkali metal carbonates and alkali metal hydroxides.

12. The process of claim 11, wherein the second non-nucleophilic base is selected from the group consisting of cesium carbonate, potassium carbonate, sodium carbonate, lithium carbonate, cesium hydroxide, potassium hydroxide, sodium hydroxide, and lithium hydroxide.

13. The process of claim 12, wherein the second non-nucleophilic base is present in amounts between about 1.0 equivalent to about 4.0 equivalents relative to the amount of cyclopropanecarboxaldehyde.

14. The process of claim 13, wherein the second non-nucleophilic base is present in amounts between about 2.0 equivalents to about 4.0 equivalents relative to the amount of cyclopropanecarboxaldehyde.

15. The process of claim 14, wherein the protic solvent is selected from the group consisting of $C_1$–$C_6$ alcohol, $H_2O$, and mixtures thereof.

16. The process of claim 15, wherein the protic solvent is $C_1$–$C_6$ alcohol.

17. The process of claim 16, wherein the protic solvent is methanol.

18. The process of claim 17, wherein a ratio of aprotic solvent to protic solvent in the reaction mixture is between about 1:1 and about 1:20.

19. The process of claim 18, wherein a ratio of aprotic solvent to protic solvent in the reaction mixture is between about 1:1 and about 1:14.

20. The process of claim 19, wherein the reaction mixture formed in step (b) is allowed to stand at about room temperature for about 15 hours to about 25 hours.

* * * * *